United States Patent [19]

Kantorski et al.

[11] 4,386,611

[45] Jun. 7, 1983

[54] TONOMETER WITH IMPROVED FLUID DISCHARGED TUBE

[75] Inventors: Joseph W. Kantorski; Robert G. Lavallee, both of Southbridge, Mass.

[73] Assignee: Warner Lambert Technologies, Inc., Southbridge, Mass.

[21] Appl. No.: 155,283

[22] Filed: Jun. 2, 1980

[51] Int. Cl.³ .............................................. A61B 3/16
[52] U.S. Cl. ...................................... 128/645; 128/648
[58] Field of Search .............. 128/648, 645; 239/590, 239/591, DIG. 21; 73/78, 81; 222/3

[56] References Cited

U.S. PATENT DOCUMENTS

| | | | |
|---|---|---|---|
| 22,574 | 1/1859 | Ostrander | 239/590 |
| 71,756 | 12/1867 | Hofer | 239/590 |
| 1,886,623 | 11/1932 | Barnes | 239/590 X |
| 2,498,596 | 2/1950 | Wallach | 222/3 |
| 2,641,839 | 6/1953 | Black | 433/80 |
| 2,723,882 | 11/1955 | Barnett | 239/591 X |
| 2,729,505 | 1/1956 | Harvey | 239/590 X |
| 3,117,726 | 1/1964 | Schöberg | 15/405 |
| 3,181,351 | 5/1965 | Stauffer | 128/645 |
| 3,232,099 | 2/1966 | Motchenbacher | 128/648 |
| 3,246,507 | 4/1966 | Hyde | 128/645 |
| 3,304,769 | 2/1967 | Stauffer | 128/648 |
| 3,538,754 | 11/1970 | Grolman et al. | 128/648 |
| 3,572,100 | 3/1971 | Grolman et al. | 128/648 |
| 3,585,849 | 6/1971 | Grolman | 128/648 |
| 3,628,526 | 12/1971 | Bigliam | 128/645 |
| 3,756,073 | 9/1973 | Lavallee et al. | 128/648 |
| 3,832,890 | 9/1974 | Grolman et al. | 128/648 |
| 3,984,054 | 10/1976 | Frochaux | 239/DIG. 21 |

FOREIGN PATENT DOCUMENTS 1294177  4/1962  France ............................. 239/590

Primary Examiner—Richard J. Apley
Assistant Examiner—J. L. Kruter
Attorney, Agent, or Firm—Alan H. Spencer

[57] ABSTRACT

A tonometer with an improved objective unit containing a fluid discharge tube having a portion thereof extending into a plenum chamber enhances the consistency of repeated regulated air discharges. The consistency is further enhanced by texturizing the inner wall of the discharge tube. Since the discharge tube extends into the plenum chamber, the objective unit can have substantial interchangeability with other tonometers.

2 Claims, 2 Drawing Figures

TONOMETER WITH IMPROVED FLUID DISCHARGED TUBE

BACKGROUND OF THE INVENTION

The present invention relates to devices for enhancing the repeatibility of consistent regulated fluid discharges and, more particularly, to discharge tubes and a method of enhancing the repeatability of regulated fluid discharges therefrom.

Devices such as non-contacting tonometers are known to require consistently repeatable regulated fluid discharges. Conventional non-contacting tonometers have a plenum chamber to receive an air pulse and a discharge tube connected to the plenum chamber for directing the air pulse toward an eyeball. The objective carrying the discharge tube of the only commercial embodiment of such devices is shown in FIG. 1. This objective has been used on commercial instruments since 1972 and has a fluid discharge tube which terminates at the junction of the tube and the objective shoulder.

Tonometer housing 1 has air passage 2 for delivering compressed air to plenum chamber 3. Plenum chamber 3 comprises a bore having stepped cylindrical walls 4, 5 and 6 with the diameter of wall 4 being less than the diameter of wall 5 which, in turn, is less than the diameter of wall 6. One end of the plenum chamber 3 is defined by window 7 which is cemented to surface 8 of housing 1. Wall 6 is defined by a portion of objective body 9. The other end of plenum chamber 3 is defined by lens surface 10 of objective doublet 11. Discharge tube 12 extends from the plane of shoulder 15 of lens retaining ring 16 through doublet 11 and front lens 13 to direct an air pulse from plenum chamber 3 toward a patient's eye (not shown). Interior wall 14 of discharge tube 12 is usually highly polished to a uniform diameter.

PRIOR ART

U.S. Pat. Nos. 3,756,073, issued Sept. 4, 1973 and 3,832,890, issued Sept. 3, 1974, have drawings illustrating non-contacting tonometers with a discharge tube which appears to extend into the plenum chamber. Both of these patents are assigned to the manufacturer of the only non-contacting tonometer utilizing an objective as generally illustrated. However, the invention of neither patent is directed toward the structure of the objective. The objective and discharge tube is only mentioned incidentally in describing the environment in which the respective inventions are intended to function.

Other patents directed to various aspects of non-contacting tonometers include:

| PATENT NO. | ISSUE DATE | INVENTOR(S) |
|---|---|---|
| 3,181,351 | 5/4/65 | N. L. Stauffer |
| 3,232,099 | 2/1/66 | C. D. Motchenbacher |
| 3,246,507 | 4/19/66 | W. L. Hyde |
| 3,304,769 | 2/21/67 | N. L. Stauffer |
| 3,538,754 | 11/10/70 | B. Grolman et al |
| 3,572,100 | 3/23/71 | B. Grolman et al |
| 3,585,849 | 6/22/71 | B. Grolman |

While each of these patents utilized a regulated air pulse discharged through an opening and an objective or a tube and usually a plenum chamber, none of the art discusses the problem of providing consistently repeatable fluid pulses in such devices although the need for consistent repeatability has always been a commercial requirement.

The prior art structure caused substantial manufacturing difficulty since it has been necessary to select a particular objective for each non-contacting tonometer by trial and error. Prior efforts to solve this problem were unsuccessful in spite of efforts to produce objectives with discharge tubes having exceedingly tight tolerances. Various modifications to the discharge tube such as tapering the end of the internal wall of the tube toward the exterior well in the vicinity of the plenum chamber have also been tried with very limited success.

BRIEF DESCRIPTION OF THE PRESENT INVENTION AND DRAWINGS

Applicants have discovered that the consistency of repeated regulated discharges can be substantially enhanced and that objective units containing a discharge tube can have substantial interchangeability if the discharge tube length is increased to extend well into the plenum chamber. The portion of the tube extending into the chamber must be of sufficient length to disrupt wavefronts produced therein. The length of the tube portion extending a into a plenum chamber may vary considerably and may be optimized for a given chamber size and shape without undue experimentation. In the commercial instrument, the preferred length of the tube portion extending into the plenum chamber is about 3/16 inches longer than the prior art tube. Consistency of the discharge is further enhanced by texturizing the interior wall of the discharge tube which is believed to create a turbulence preventing laminar air flow through the discharge tube.

The method of the present invention includes the steps of increasing the length of a discharge tube extending into a plenum chamber and roughening the interior wall thereof to effect enhanced consistency of fluid discharges therethrough.

DESCRIPTION OF THE PREFERRED EMBODIMENT

Figure 1:
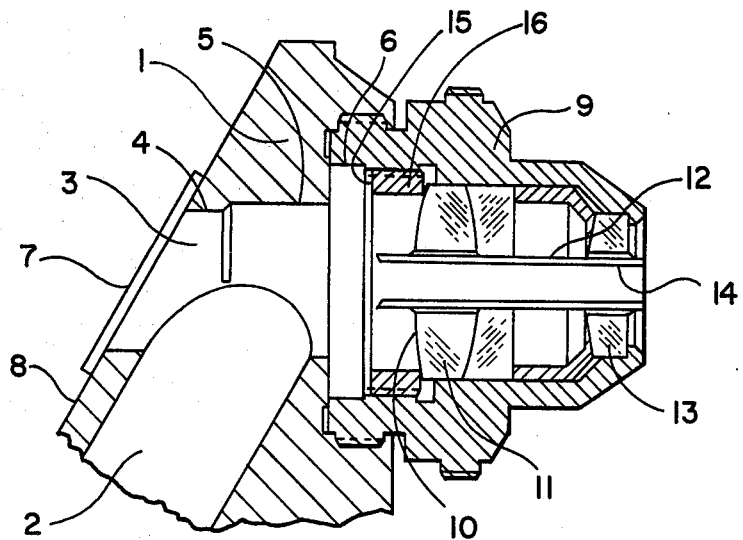
FIG. 1 is a side view in cross-section illustrating the structure of prior art devices having a discharge tube.
Figure 2:
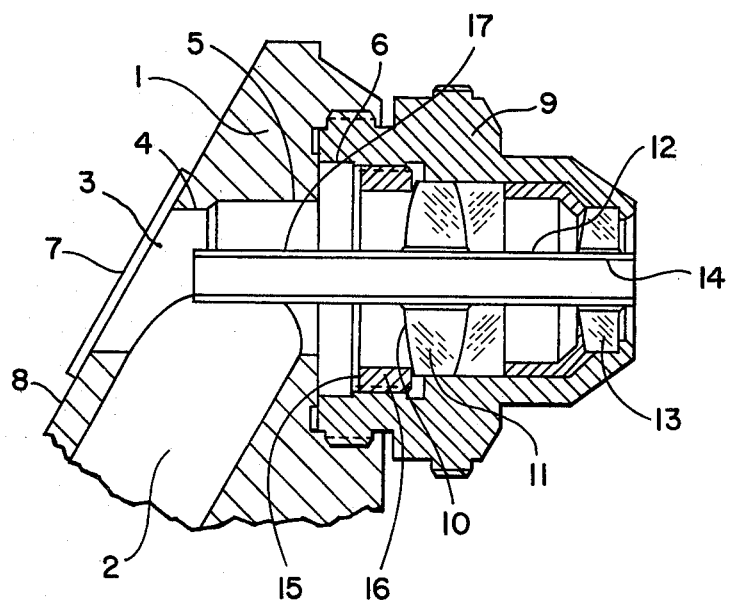
FIG. 2 is a side view in cross-section illustrating the structure of the preferred embodiment of the present invention.

Referring to FIG. 2, similar components have the same numerical identification as the components of FIG. 1. Discharge tube 12 has its length increased by portion 17 to extend past shoulder 10 into plenum chamber 3. In the preferred embodiment, portion 17 is nearly 40% of the total length of discharge tube 12. One discharge tube 12 found to be particularly satisfactory has a total length (including portion 17) of 1.075", an inside diameter of 0.095" with a wall thickness of about 0.0125".

To further enhance the consistency of the air pulse discharges through discharge tube 12, interior wall 14 should be texturized. For example, the preferred embodiment described above was texturized by sand blasting using silicon carbide having a 50 micron particle size ejected through a 0.031 diameter nozzle at 90 PSI.

To demonstrate the improved performance of discharge tubes according to the present invention, a comparison test was run using seven production non-contacting tonometers commercially available under Catalog No. 12415 from American Optical Corporation.

Five objectives fitted with prior art discharge tubes with an overall length of 0.654", and I.D. of 0.095" as illustrated in FIG. 1 were tested in each of the instruments. Six objectives each having discharge tubes with the dimensions of the preferred embodiment noted above were also tested in each of the seven instruments using a test fixture for providing standard low, medium, and high readings on a tonometer; fifteen readings were taken with each objective on each instrument (five low, five medium, and five high). Table 1 reports the results of the mean of standard deviations and the standard deviation of means for each group of readings.

TABLE I

| Instrument | | Mean of Standard Deviations | | Standard Deviation of Means | |
|---|---|---|---|---|---|
| | | Prior Art | Present Invention | Prior Art | Present Invention |
| XX XXXX1 | Low | 0.70 | .50 | .26 | .28 |
| | Medium | .88 | .44 | .26 | .21 |
| | High | 1.30 | .82 | .56 | .42 |
| XX XXXX2 | Low | .63 | .39 | .30 | .20 |
| | Medium | .88 | .51 | .36 | .10 |
| | High | 1.67 | .98 | .77 | .29 |
| XX XXXX3 | Low | .82 | .70 | .21 | .38 |
| | Medium | 1.09 | .58 | .15 | .38 |
| | High | 1.34 | 1.11 | .64 | .31 |
| XX XXXX4 | Low | .76 | .40 | .29 | .30 |
| | Medium | 1.14 | .43 | .30 | .50 |
| | High | 1.73 | .79 | 2.79 | .80 |
| XX XXXX5 | Low | .71 | .39 | .26 | .15 |
| | Medium | 1.20 | .73 | .22 | .15 |
| | High | 1.43 | 1.00 | .19 | .34 |
| XX XXXX6 | Low | .69 | .53 | .36 | .30 |
| | Medium | .84 | .59 | .64 | .36 |
| | High | 1.91 | 1.18 | 4.60 | .59 |
| XX XXXX7 | Low | .76 | .35 | .22 | .14 |
| | Medium | .92 | .59 | .18 | .27 |
| | High | 1.07 | .71 | .48 | .60 |

What is claimed is:

1. A non-contacting tonometer including a plenum chamber, an objective means having a discharge tube, means for delivering compressed air to the chamber, a portion of said discharge tube extending into said chamber, said portion being effective to disrupt wavefronts affecting the uniformity of repeated air pulses discharged through said discharge tube, wherein said objective means is interchangeable in other non-contacting tonometers.

2. The device according to claim 1 wherein said tube has an inner wall uniformly textured to a depth effective to prevent laminar air flow through said tube.

* * * * *